United States Patent [19]

Takago et al.

[11] Patent Number: 5,196,557
[45] Date of Patent: Mar. 23, 1993

[54] ORGANIC SILICON COMPOUNDS AND METHOD FOR MAKING

[75] Inventors: Toshio Takago; Hirofumi Kishita; Shinichi Sato; Hideki Fujii, all of Annaka, Japan

[73] Assignee: Shin-Etsu Chemical Company Limited, Tokyo, Japan

[21] Appl. No.: 889,875

[22] Filed: May 29, 1992

[30] Foreign Application Priority Data

May 29, 1991 [JP] Japan ................... 3-153944

[51] Int. Cl.$^5$ .............................. C07F 7/10
[52] U.S. Cl. .................................... 556/422
[58] Field of Search .......................... 556/422

[56] References Cited

U.S. PATENT DOCUMENTS

| | | |
|---|---|---|
| 3,478,076 | 11/1969 | Kim et al. .............. 556/422 X |
| 3,639,156 | 2/1972 | Pittman et al. .......... 556/422 X |
| 3,647,740 | 3/1972 | Soree et al. ............ 556/422 X |
| 3,681,418 | 8/1972 | Pierce et al. ........... 556/422 X |
| 3,729,445 | 4/1973 | Smith et al. ............ 556/422 X |
| 3,859,320 | 1/1975 | Atherton ................ 556/422 |
| 3,903,123 | 9/1975 | Deiner et al. ........... 556/422 X |
| 5,124,467 | 6/1992 | Rodgers et al. .......... 556/422 X |

Primary Examiner—Paul F. Shaver
Attorney, Agent, or Firm—Millen, White, Zelano and Branigan

[57] ABSTRACT

Organic silicon compounds of formula (1) are novel:

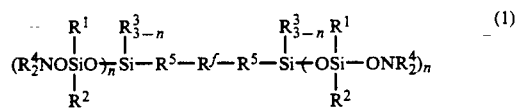

In the formula, $R^1$, $R^2$ and $R^3$ are monovalent $C_{1-8}$ hydrocarbon group, $R^4$ is a $C_{1-6}$ alkyl group, $R^5$ is a $C_{2-6}$ alkylene group or a $C_{2-6}$ alkylene group containing at least one —C—O—C— linkage, Rf is a $C_{1-12}$ perfluoroalkylene or perfluorocyclo-alkylene group or a $C_{1-12}$ perfluoroalkylene or perfluorocycloalkylene group containing at least one —C—O—C— linkage, and n is 1, 2 or 3. The organic silicon compounds are useful source materials for the manufacture of fluorinated polysiloxanes having solvent resistance, chemical resistance and release property.

12 Claims, 3 Drawing Sheets

ORGANIC SILICON COMPOUNDS AND METHOD FOR MAKING

This invention relates to novel organic silicon compounds having a fluorinated alkylene group in the backbone and an organoaminoxy group at either end and a process for preparing the same.

BACKGROUND OF THE INVENTION

In the prior art, polysiloxanes containing fluorine atoms are well known as source materials for the manufacture of solvent resistant, chemically resistant rubber materials and source materials for the manufacture of mold release agents, water repellent agents and oil repellent agents.

A variety of polysiloxanes containing fluorine atoms have been proposed as well as compounds for introducing fluorine atoms into polysiloxanes. There is a need for a compound which can more easily and effectively introduce fluorine atoms into polysiloxanes such that the characteristics of fluorine atoms are exerted.

An object of the present invention is to provide an organic silicon compound which is useful as a source material from which polysiloxanes having improved properties including solvent resistance, chemical resistance and mold release properties are prepared in a relatively simple manner.

SUMMARY OF THE INVENTION

The inventors have found that a novel organic silicon compound having a fluorinated alkylene group in the backbone and terminated with an organoaminoxy group at each end as represented by formula (1) below is obtained by effecting a dehydrogenation reaction between a compound of formula (2) below and a diorgano-hydroxyamine.

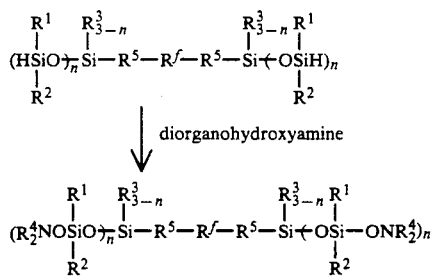

In formula (1), $R^1$, $R^2$ and $R^3$ are independently selected from monovalent hydrocarbon groups having 1 to 8 carbon atoms, $R^4$ is an alkyl group having 1 to 6 carbon atoms, $R^5$ is an alkylene group having 2 to 6 carbon atoms or an alkylene group having 2 to 6 carbon atoms and containing at least one —C—O—C— linkage, Rf is selected from the group consisting of perfluoroalkylene and perfluorocycloalkylene groups having 1 to 12 carbon atoms and perfluoroalkylene and perfluorocycloalkylene groups having 1 to 20 carbon atoms and containing at least one —C—O—C— linkage, and letter n is equal to 1, 2 or 3.

This novel organic silicon compound includes an organoaminoxy group at each terminal which is susceptible to condensation with a silanol compound. Therefore, fluorine atoms or a fluorine-containing alkylene group can be readily introduced into a silanol-containing organopolysiloxane by condensing the organoaminoxy group of the organic silicon compound with a silanol group of the organopolysiloxane. The organic silicon compound is effective as a chain extender when it contains two organoaminoxy groups, that is, difunctional, and as a crosslinking agent when it contains three or more organoaminoxy groups, that is, trifunctional or polyfunctional, as shown in schemes A and B.

Scheme A

Condensation reaction associated with the introduction of organic silicon compound into organopolysiloxane as a chain extender.

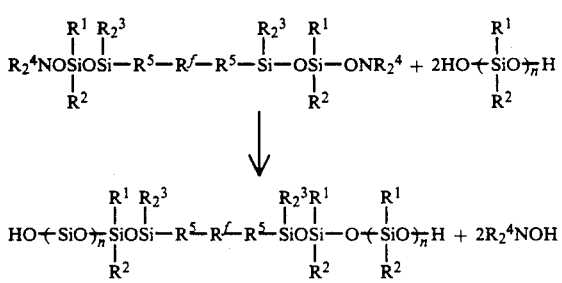

Scheme B

Condensation reaction associated with the introduction of organic silicon compound into organopolysiloxane as a crosslinking agent.

As in scheme A, removal of $R_2^4NOH$ occurs between $\equiv SiOH$ and $R_2^4NOSi\equiv$, resulting in $\equiv SiOSi\equiv + R_2^4NOH$.

Accordingly, the present invention in a first aspect provides an organic silicon compound of formula (1) which is useful as a source material for manufacturing a polysiloxane having fluorine atoms introduced into its backbone by condensing the compound with a silanol compound.

In a second aspect, there is provided a process for preparing an organic silicon compound of formula (1) by effecting dehydrogenation reaction between a compound of formula (2) and a diorganohydroxyamine.

DETAILED DESCRIPTION OF THE INVENTION

Figure 1:
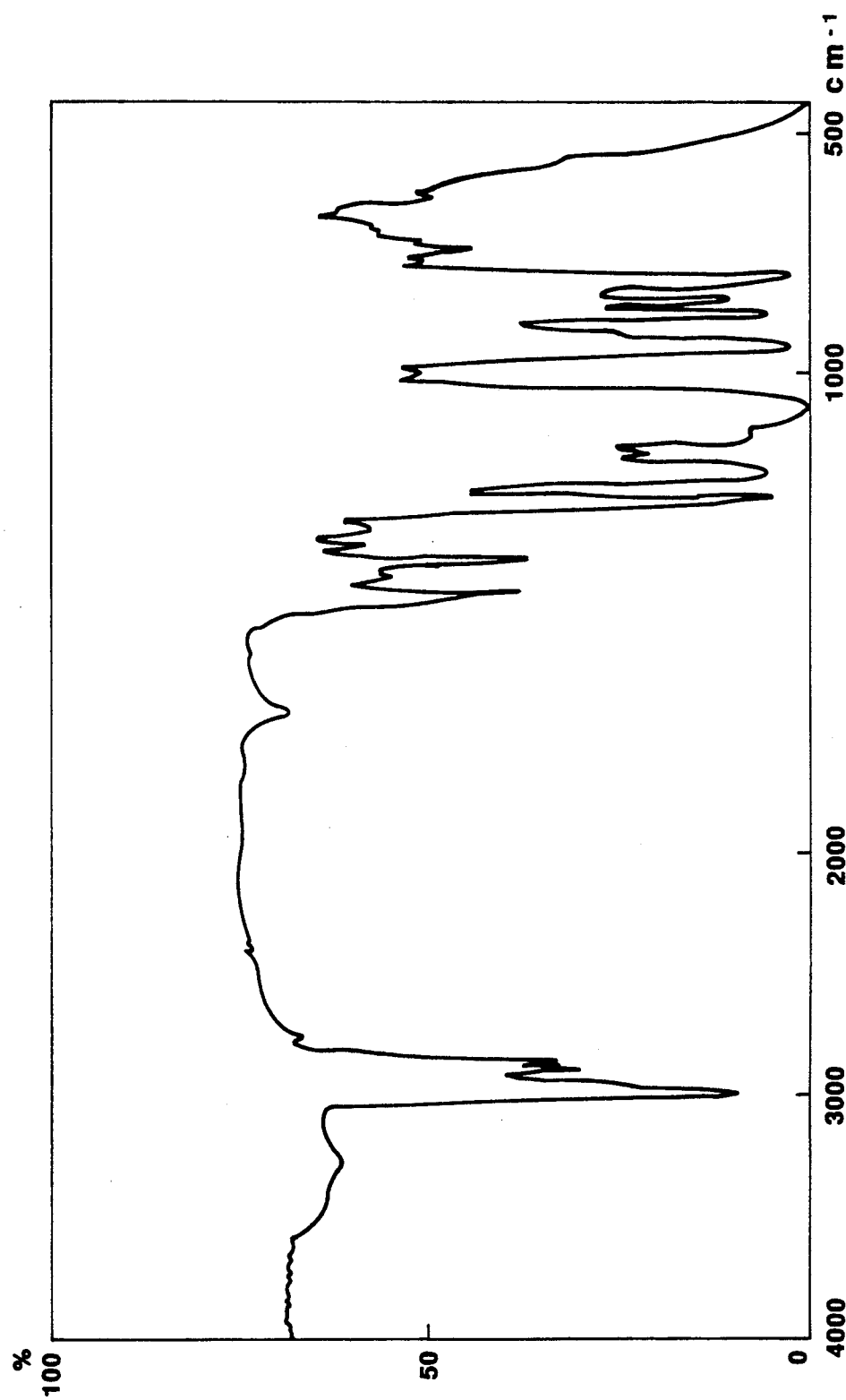
FIGS. 1, 2 and 3 are charts illustrating the IR absorption spectrum of the organic silicon compounds prepared in Examples 1, 2 and 3, respectively.

The organic silicon compounds according to the present invention are of the following general formula (1).

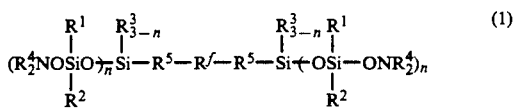

$R^1$, $R^2$ and $R^3$, which may be the same or different, are independently selected from monovalent hydrocarbon groups having 1 to 8 carbon atoms, preferably 1 to 6 carbon atoms, for example, alkyl groups such as methyl, ethyl, propyl, butyl and hexyl groups, cycloalkyl groups such as a cyclohexyl group, alkenyl groups such as vinyl and allyl groups, and aryl groups such as a tolyl group.

$R^4$ is an alkyl group having 1 to 6 carbon atoms, preferably 1 to 4 carbon atoms.

$R^5$ is selected from the group consisting of an alkylene group having 2 to 6 carbon atoms, preferably 2 to 3 carbon atoms and an alkylene group containing one or more (preferably 1 to 6) —C—O—C— linkages and having 2 to 6 carbon atoms, preferably 2 to 3 carbon atoms, for example, —CH$_2$CH$_2$— and —CH$_2$CH$_2$OCH$_2$—.

Rf is selected from the group consisting of perfluoroalkylene and perfluorocycloalkylene groups having 1 to 12 carbon atoms, preferably 2 to 8 carbon atoms and perfluoroalkylene and perfluorocycloalkylene groups containing one or more (preferably 1 to 6) —C—O—C— linkages and having 1 to 20 carbon atoms, preferably 6 to 15 carbon atoms. Examples of the Rf group are shown below.

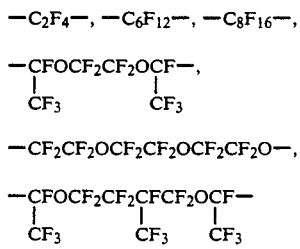

Letter n is equal to 1, 2 or 3.

The organic silicon compounds of the invention can be prepared, for example, by effecting a dehydrogenation reaction between compounds of formula (2) and diorganohydroxyamines of formula (3).

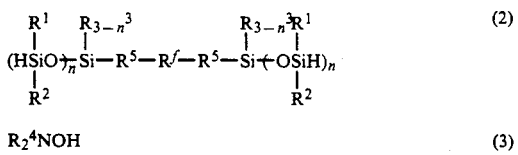

In formulae (2) and (3), $R^1$ to $R^5$, Rf, and n are as defined above.

The compounds of formula (2) can be prepared by cooling a mixture of a compound of the following formula (4), conc. hydrochloric acid and water, adding a compound of the following formula (5) to the mixture, cooling the mixture to room temperature, followed by agitation, separation, neutralization, water washing and distillation.

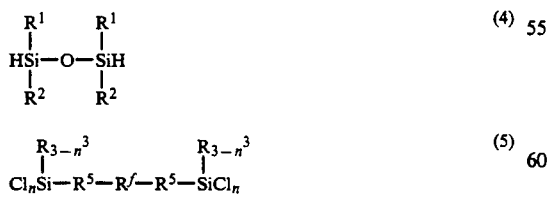

In formulae (4) and (5), $R^1$, $R^2$, $R^3$, $R^5$, Rf, and n are as defined above.

For obtaining the compound of the invention, the diorganohydroxyamine of formula (3) is added dropwise to the compound of formula (2). The amount of the diorganohydroxyamine of formula (3) added is preferably from 1 to 5 mol, especially from 1.1 to 1.5 mol per mol of ≡SiH o in the compound of formula (2). The preferred reaction conditions include a temperature of 0° to 100° C., especially 10° to 40° C. and a time of about 1 to 8 hours, especially about 2 to 4 hours. This reaction can be carried out without a solvent by directly adding dropwise the diorganohydroxyamine of formula (3) to the compound of formula (2) although it is also possible to dissolve the compound of formula (2) in a solvent which does not impede the reaction, for example, benzene, toluene, xylene, n-hexane, cyclohexane and tetrahydrofuran, and adding dropwise the diorganohydroxyamine of formula (3) to the solution if desired.

When the addition of diorganohydroxyamine is complete, the reaction solution is cooled down to room temperature and agitated for about 1 to 24 hours, preferably about 4 to 16 hours. Removal of the unreacted diorganohydroxyamine or a low-boiling fraction by stripping yields an organic silicon compound of formula (1). It is to be noted that since the organic silicon compound is hydrolyzable, a series of steps including addition of diorganohydroxyamine should preferably be carried out in an inert gas atmosphere such as nitrogen and argon.

The organic silicon compounds of formula (1) can condense with organopolysiloxanes having a silanol group under conventional condensation conditions as previously shown by schemes A and B, thus introducing fluorine atoms into the organopolysiloxanes.

EXAMPLE

Examples of the present invention are given below by way of illustration and not by way of limitation.

First described is the preparation of compounds of formula (2), from which organic silicon compounds of the present invention are prepared.

REFERENCE EXAMPLE 1

A 4-liter, three necked flask equipped with a reflux condenser, thermometer, dropping funnel and magnetic stirrer was charged with 2,666 grams (17.9 mol) of H(CH$_3$)$_2$SiOSi(CH$_3$)$_2$H, 995 grams of conc. hydrochloric acid, and 398 grams of water and cooled to 10° C. with an ice water bath. The mixture was dissolved in 1,000 grams of metaxylene hexafluoride. To the solution, 2,240 grams (3.6 mol) of Cl$_3$SiCH$_2$CH$_2$C$_6$F$_{12}$CH$_2$CH$_2$SiCl$_3$ was added dropwise at a temperature of 10° to 15° C. At the end of addition, the reaction mixture was agitated at room temperature for one hour, followed by separation, neutralization, water washing, and distillation. There was obtained 2,813 grams (yield 91%) of a fraction having a boiling point of 155° to 158° C./1×10$^{-5}$ Torr. On analysis by $^1$H-NMR spectroscopy, IR absorption spectroscopy and elemental analysis, the fraction was identified to be a compound of the following formula (6).

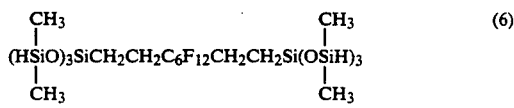

REFERENCE EXAMPLE 2

A 3-liter, three necked flask equipped with a reflux condenser, thermometer, dropping funnel and magnetic stirrer was charged with 914.0 grams (6.82 mol) of H(CH₃)₂SiOSi(CH₃)₂H, 140.0 grams of conc. hydrochloric acid, and 56.0 grams of water and cooled to 10° C. with an ice water bath. To the mixture, 1,000 grams of a compound of the following formula (7):

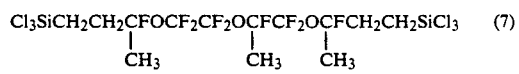

was added dropwise at a temperature of 10° to 15° C. At the end of addition, the reaction mixture was agitated at room temperature for one hour, followed by separation, neutralization, water washing, and distillation. There was obtained 1316.5 grams (yield 90%) of a fraction having a boiling point of 160° to 162° C./1×10⁻⁵ Torr. On analysis by ¹H-NMR spectroscopy, IR absorption spectroscopy and elemental analysis, the fraction was identified to be a compound of the following formula (8).

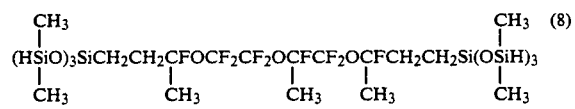

EXAMPLE 1

A 5-liter, three necked flask equipped with a reflux condenser connected to a calcium chloride tube, thermometer, dropping funnel connected to a gas inlet tube, and magnetic stirrer was charged with 2,000 grams (2.3 mol) of the compound of formula (6) obtained in Reference Example 1. With stirring under nitrogen stream, 1,363 grams (15.3 mol) of diethylhydroxyamine was added dropwise to the flask. During addition, the flask was cooled with an ice water bath to an internal temperature of 20° to 40° C. At the end of addition of diethylhydroxyamine, the mixture was agitated for 12 hours at room temperature. Removal of a low-boiling fraction by stripping left 3,133 grams (yield 98%) of a product. Its IR absorption spectrum is shown in FIG. 1 and the results of its ¹H-NMR spectroscopy and elemental analysis are shown in Tables 1 and 2. The product was thus identified to be an organic silicon compound of the following formula (9).

TABLE 1

| Proton NMR | |
|---|---|
| δ (ppm) | |
| 0.20 | s, Si—CH₃, 36H |
| 0.93–1.16 | m, —CH₃, 36H |

TABLE 1-continued

| Proton NMR | |
|---|---|
| δ (ppm) | |
| 2.60–2.97 | m, —CH₂—, 24H |

TABLE 2

| | Elemental analysis | | | | | |
|---|---|---|---|---|---|---|
| | C | H | Si | F | O | N |
| Calcd., % | 39.9 | 7.5 | 16.2 | 16.5 | 13.9 | 6.0 |
| Found, % | 40.0 | 7.3 | 16.2 | 16.6 | 13.8 | 6.1 |

$$((C_2H_5)_2NO\underset{CH_3}{\overset{CH_3}{Si}O})_3SiCH_2CH_2C_6F_{12}CH_2CH_2Si(O\underset{CH_3}{\overset{CH_3}{Si}}ON(C_2H_5)_2)_3 \quad (9)$$

EXAMPLE 2

Figure 2:
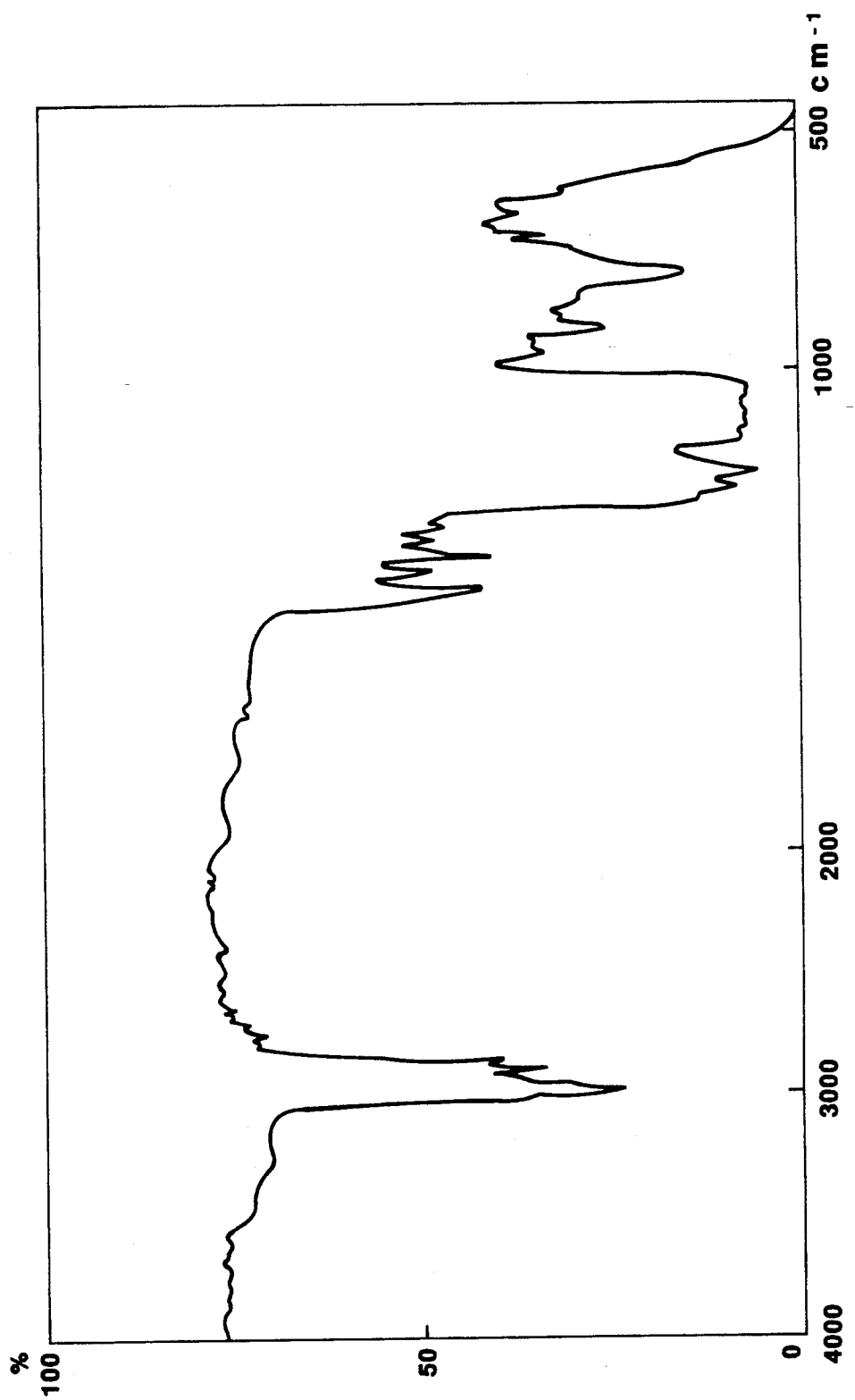

A 3-liter, three necked flask equipped with a reflux condenser connected to a calcium chloride tube, thermometer, dropping funnel connected to a gas inlet tube, and magnetic stirrer was charged with 1,000 grams (0.94 mol) of the compound of formula (8) obtained in Reference Example 2. With stirring under nitrogen stream, 552.2 grams (6.20 mol) of diethylhydroxyamine was added dropwise to the flask. During addition, the flask was cooled with an ice water bath to an internal temperature of 20° to 40° C. At the end of addition of diethydroxyamine, the mixture was agitated for 12 hours at room temperature. Removal of a low-boiling fraction by stripping left 1353.2 grams (yield 91%) of a product. Its IR absorption spectrum is shown in FIG. 2 and the results of its ¹H-NMR spectroscopy and elemental analysis are shown in Tables 3 and 4. The product was thus identified to be an organic silicon compound of the following formula (10).

TABLE 3

| Proton NMR | |
|---|---|
| δ (ppm) | |
| 0.20 | s, Si—CH₃, 36H |
| 0.92–1.16 | m, —CH₃, 36H |
| 2.62–2.99 | m, —CH₂—, 24H |

TABLE 4

| | Elemental analysis | | | | | |
|---|---|---|---|---|---|---|
| | C | H | Si | F | O | N |
| Calcd., % | 37.2 | 6.6 | 14.2 | 21.6 | 15.1 | 5.3 |
| Found, % | 37.2 | 6.8 | 14.3 | 21.5 | 14.9 | 5.3 |

$$((C_2H_5)_2NO\underset{CH_3}{\overset{CH_3}{Si}O})_3SiCH_2CH_2\underset{CF_3}{CF}OCF_2CF_2O\underset{CF_3}{CF}CF_2O\underset{CF_3}{CF}CH_2CH_2Si(O\underset{CH_3}{\overset{CH_3}{Si}}ON(C_2H_5)_2)_3 \quad (10)$$

EXAMPLE 3

A 1-liter, three necked flask equipped with a reflux condenser connected to a calcium chloride tube, thermometer, dropping funnel connected to a gas inlet tube, and magnetic stirrer was charged with 500 grams (0.61 mol) of a compound of the following formula (11).

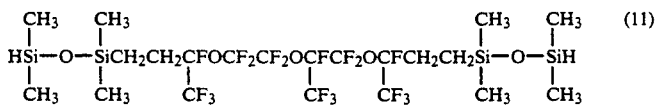

Figure 3:
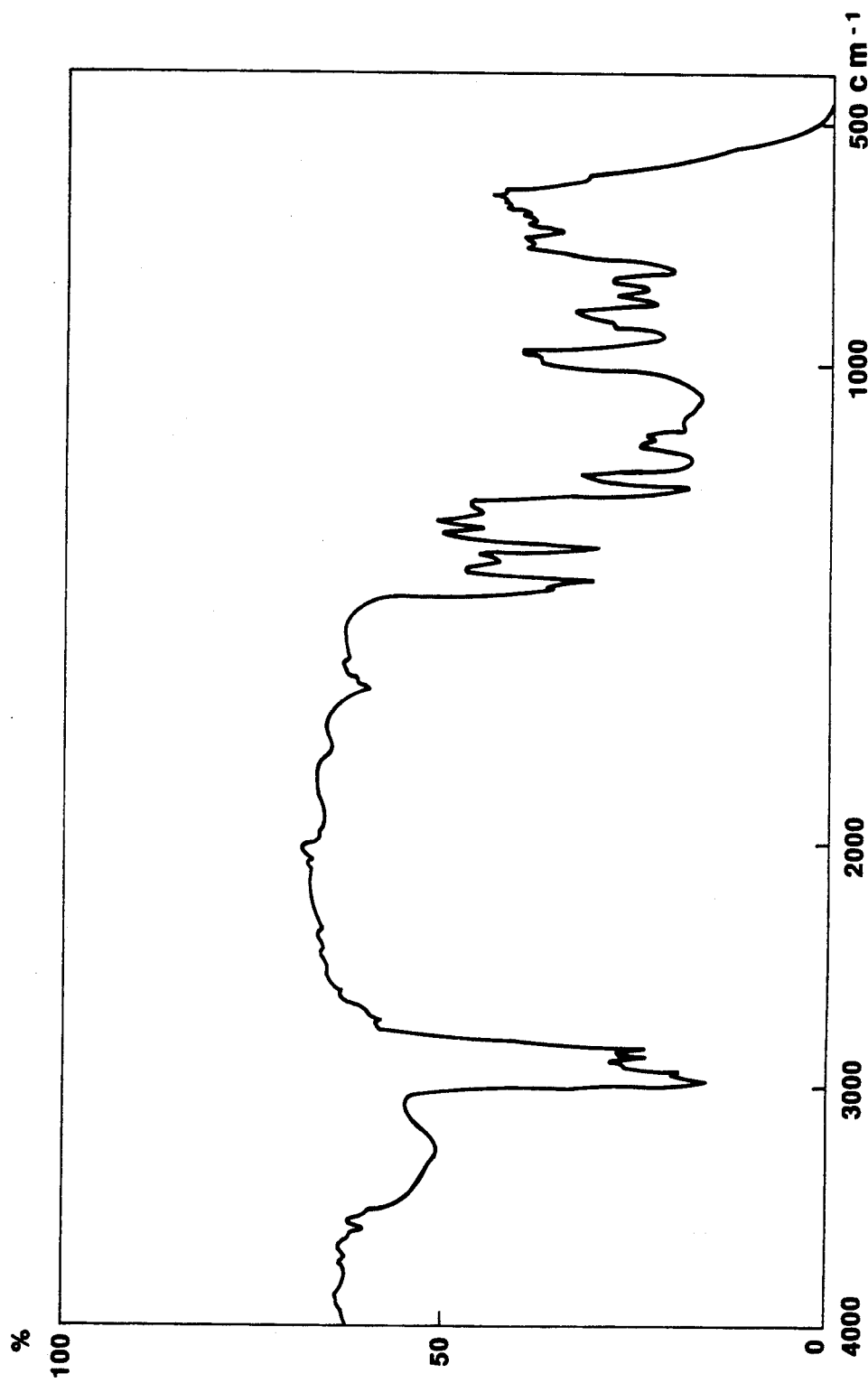

With stirring under nitrogen stream, 119.4 grams (1.34 mol) of diethylhydroxyamine was added dropwise to the flask. During addition, the flask was cooled with an ice water bath to an internal temperature of 20° to 40° C. At the end of addition of diethylhydroxyamine, the mixture was agitated for 12 hours at room temperature. Removal of a low-boiling fraction by stripping left 878 grams (yield 97%) of a non-volatile matter. Its IR absorption spectrum is shown in FIG. 3 and the results of its $^1$H-NMR spectroscopy and elemental analysis are shown in Tables 5 and 6. The product was thus identified to be an organic silicon compound of the following formula (12).

TABLE 5

| δ (ppm) | Proton NMR |
|---|---|
| 0.20 | s, Si—CH$_3$, 24H |
| 0.93-1.15 | m, —CH$_3$, 12H |
| 2.61-2.99 | m, —CH$_2$—, 8H |

TABLE 6

| | \multicolumn{6}{c}{Elemental analysis} | | | | | |
|---|---|---|---|---|---|---|
| | C | H | Si | F | O | N |
| Calcd., % | 35.0 | 5.2 | 11.3 | 34.4 | 11.3 | 2.8 |
| Found, % | 34.8 | 5.2 | 11.4 | 34.1 | 11.6 | 2.9 |

$$(C_2H_5)_2NO\underset{\underset{CH_3}{|}}{\overset{\overset{CH_3}{|}}{Si}}-O-\underset{\underset{CH_3}{|}}{\overset{\overset{CH_3}{|}}{Si}}CH_2CH_2\underset{\underset{CF_3}{|}}{CF}OCF_2CF_2O\underset{\underset{CF_3}{|}}{CF}CF_2O\underset{\underset{CF_3}{|}}{CF}CH_2CH_2\underset{\underset{CH_3}{|}}{\overset{\overset{CH_3}{|}}{Si}}-O-\underset{\underset{CH_3}{|}}{\overset{\overset{CH_3}{|}}{Si}}ON(C_2H_5)_2 \quad (12)$$

The novel organic silicon compounds of the present invention have a fluorinated alkylene group in their backbone and an organoaminoxy group at each end which is susceptible to condensation with a silanol compound. Simply by carrying out condensation reaction between the organic silicon compound and a polysiloxane having a silanol group, fluorine atoms or fluorinated alkylene group can be effectively introduced into the polysiloxane backbone, imparting the characteristics of fluorine to the organopolysiloxane. Organic silicon compounds having two organoaminoxy groups act as chain extenders and those having three or more organoaminoxy groups act as crosslinking agents. Polysiloxanes which are chain extended or crosslinked with the organic silicon compounds of the invention exhibit characteristics inherent to fluorine introduced. The organic silicon compounds of the invention are useful as source materials for the manufacture of polysiloxanes and other organic resins which are required to have solvent resistance, chemical resistance, water repellency, oil repellency and lubricity.

The process of the present invention can produce such useful compounds in a simple efficient manner.

While the invention has been described in what is presently considered to be a preferred embodiment, other variations and modifications will become apparent to those skilled in the art. It is intended, therefore, that the invention not be limited to the illustrative embodiments, but be interpreted within the full spirit and scope of the appended claims.

We claim:
1. An organic silicon compound of the following formula (1):

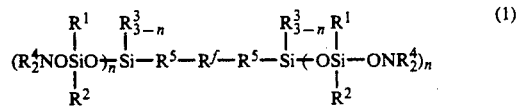

wherein R$^1$, R$^2$ and R$^3$ are independently selected from monovalent hydrocarbon groups having 1 to 8 carbon atoms, R$^4$ is an alkyl group having 1 to 6 carbon atoms, R$^5$ is an alkylene group having 2 to 6 carbon atoms or an alkylene group having 2 to 6 carbon atoms and containing at least one —C—O—C— linkage, Rf is selected from the group consisting of perfluoroalkylene and perfluorocycloalkylene groups having 1 to 12 carbon atoms and perfluoroalkylene and perfluorocycloalkylene groups having 1 to 20 carbon atoms and containing at least one —C—O—C— linkage, and letter n is equal to 1, 2 or 3.

2. A process for preparing an organic silicon compound of the following formula (1):

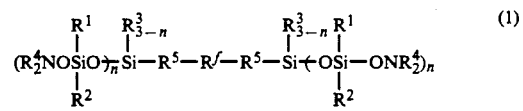

wherein R$^1$, R$^2$ and R$^3$ are independently selected from monovalent hydrocarbon groups having 1 to 8 carbon atoms, R$^4$ is an alkyl group having 1 to 6 carbon atoms, R$^5$ is an alkylene group having 2 to 6 carbon atoms or an alkylene group having 2 to 6 carbon atoms and containing at least one —C—O—C— linkage, Rf is selected from the group consisting of perfluoroalkylene and perfluorocycloalkylene groups having 1 to 12 carbon atoms and perfluoroalkylene and perfluorocycloalkylene groups having 1 to 20 carbon atoms and containing at least one —C—O—C— linkage, letter n is equal to 1, 2 or 3, said process comprising the step of effecting a dehydrogenation reaction between a compound of the following formula (2):

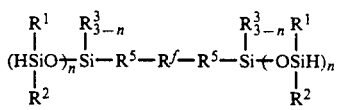  (2)

wherein $R^1$, $R^2$, $R^3$, $R^5$, Rf, and n are as defined above and a diorganohydroxyamine of the following formula (3):

$$R_2^4NOH \qquad (3)$$

wherein $R^4$ is as defined above.

3. The organic silicon compound of claim 1, wherein $R^1$, $R^2$ and $R^3$ are independently selected from the group consisting of methyl, ethyl, propyl, butyl, hexyl, cyclohexyl, vinyl, allyl and tolyl groups.

4. The organic silicon compound of claim 1, wherein $R^5$ is selected from the group consisting of an alkylene group having 2 to 3 carbon atoms and an alkylene group containing 1 to 6 —C—O—C— linkages and 2 to 6 carbon atoms.

5. The organic silicon compound of claim 1, wherein Rf is selected from the group consisting of perfluoroalkylene and perfluorocycloalkylene groups having 2 to 8 carbon atoms and perfluoroalkylene and perfluorocycloalkylene groups containing 1 to 6 —C—O—C— linkages and 6 to 15 carbon atoms.

6. The organic silicon compound of claim 1, wherein Rf is a perfluoroalkylene or perfluorocycloalkylene group having 1 to 6 —C—O—C— linkages.

7. The process of claim 2, wherein the diorganohydroxyamine is added in an amount of from 1 to 5 mol per mol of $\equiv$SiH groups in the compound of formula (2).

8. The process of claim 7, wherein 1.1 to 1.5 mol of diorganohydroxyamine is used per mol of $\equiv$SiH groups.

9. The process of claim 2, wherein the dehydrogenation reaction is carried out at a temperature of 0-100° C. for 1 to 8 hours.

10. The process of claim 9, wherein the temperature is 10° to 40° C. and the time is 2 to 4 hours.

11. The process of claim 2, wherein the diorganohydroxyamine is added dropwise to the compound of formula (2) and no solvent is used.

12. The process of claim 2, wherein the diorganohydroxyamine is added dropwise to the compound of formula (2) which is dissolved in a solvent which does not impede the reaction.

* * * * *